United States Patent [19]

Eberhard et al.

[11] Patent Number: 5,032,990
[45] Date of Patent: Jul. 16, 1991

[54] TRANSLATE ROTATE SCANNING METHOD FOR X-RAY IMAGING

[75] Inventors: Jeffrey W. Eberhard; Kwok C. Tam, both of Schenectady, N.Y.

[73] Assignee: General Electric Company, Schenectady, N.Y.

[21] Appl. No.: 357,914

[22] Filed: May 30, 1989

[51] Int. Cl.⁵ .......................... G06F 15/00; A61B 6/00
[52] U.S. Cl. .......................... 364/413.15; 364/413.13; 364/413.14; 364/413.19; 378/4; 378/901
[58] Field of Search ...................... 364/413.13, 413.15, 364/413.19; 378/901, 4

[56] References Cited

U.S. PATENT DOCUMENTS

| | | | |
|---|---|---|---|
| 4,630,202 | 12/1989 | Mori | 364/413.15 |
| 4,803,639 | 2/1989 | Steele et al. | 364/507 |
| 4,888,693 | 12/1989 | Tam | 364/413.13 |
| 4,894,775 | 1/1990 | Kritchman et al. | 364/413.16 |
| 4,907,157 | 3/1990 | Uyama et al. | 364/413.13 |

OTHER PUBLICATIONS

K. C. Tam, "Reducing the Fan-Beam Scanning Angular Range" Phys. Med. Biol., 1988, vol. 33, No. 8, 955-967.

*Primary Examiner*—Michael R. Fleming
*Assistant Examiner*—X. Chung
*Attorney, Agent, or Firm*—Marilyn Glaubensklee; James C. Davis, Jr.; Paul R. Webb, II

[57] ABSTRACT

Rapid x-ray inspection of objects larger than an x-ray detector array is based on a translate rotate scanning motion of the object relative to the fan beam source and detector. The scan for computerized tomography imaging is accomplished by rotating the object through 360 degrees at two or more positions relative to the source and detector array; in moving to another position the object is rotated and the object or source and detector are translated. A partial set of x-ray data is acquired at every position which are combined to obtain a full data set for complete image reconstruction. X-ray data for digital radiography imaging is acquired by scanning the object vertically at a first position at one view angle, rotating and translating the object relative to the source and detector to a second position, scanning vertically, and so on to cover the object field of view, and combining the partial data sets.

16 Claims, 6 Drawing Sheets

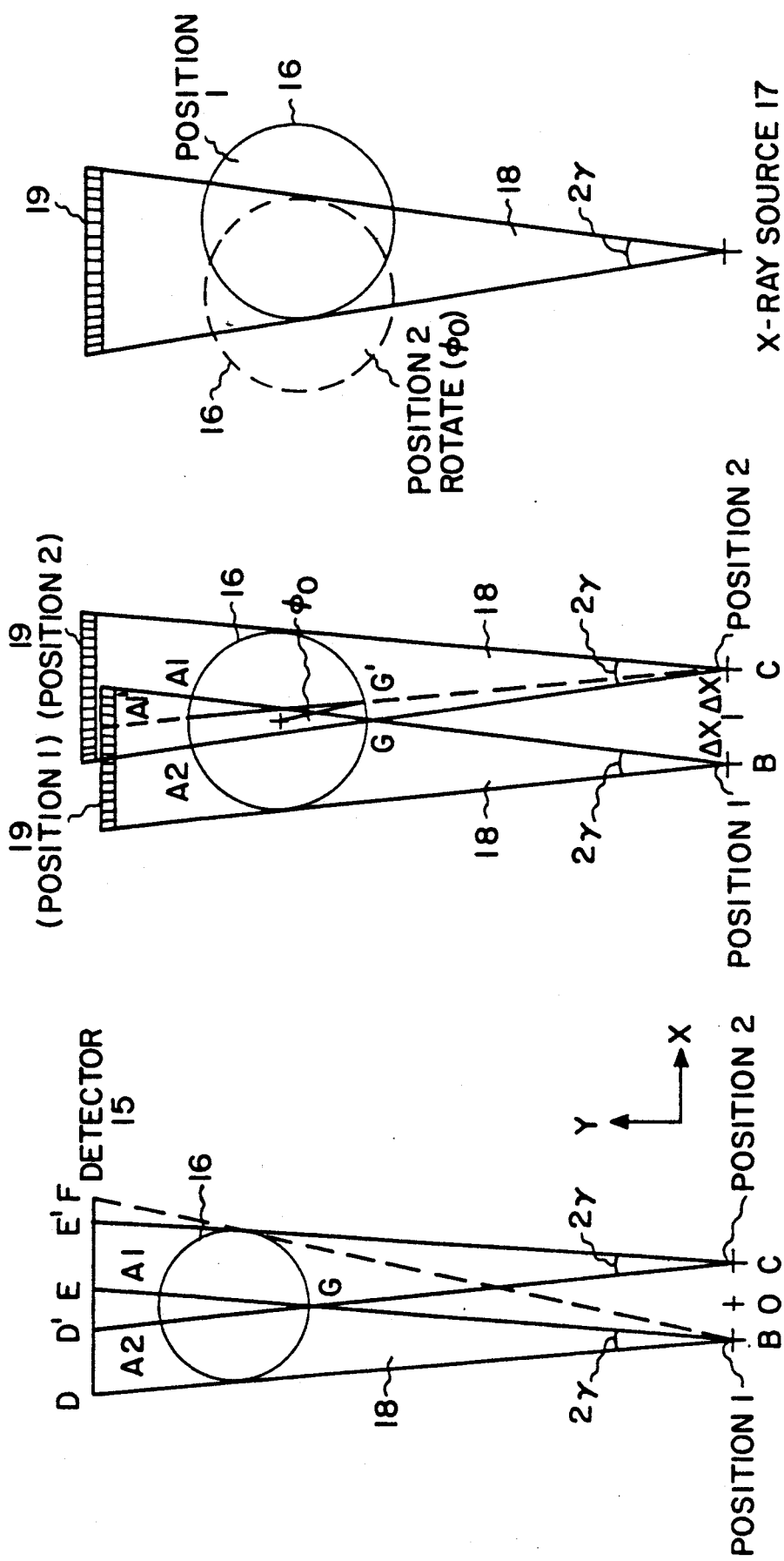

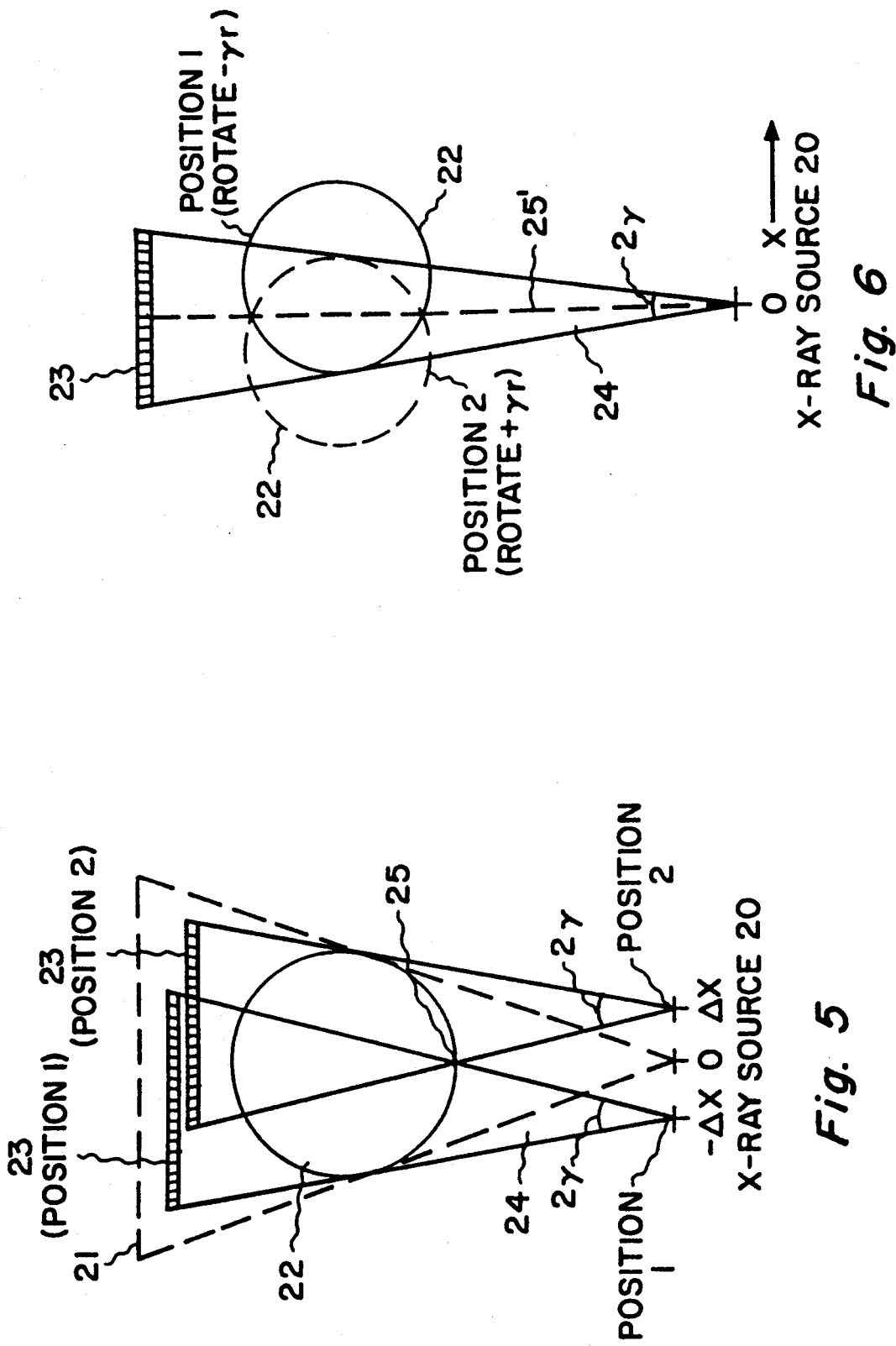

TRANSLATE ROTATE SCANNING METHOD FOR X-RAY IMAGING

BACKGROUND OF THE INVENTION

This invention relates to a method of scanning and imaging objects that are larger than a detector array, and more particularly to a translate rotate scanning motion for digital radiography (DR) and computerized tomography (CT) imaging.

Rapid inspection of large industrial parts is becoming increasingly critical as manufacturing moves from assembly of small parts to utilization of large castings. In order to meet typical spatial resolution requirements, detectors with many thousands of individual elements are becoming necessary. In addition, as high resolution scanning capabilities and requirements grow, inspection of even small parts can require thousands of detector elements. Fabrication requirements, however, limit the number of individual elements that can be assembled into a single detector. The problem presented is to create a scanning configuration that can synthesize large arrays of detector elements from smaller arrays in a rapid, efficient manner, and to devise image reconstruction algorithms which make use of these data in an optimum fashion.

CT imagers have evolved through several generations of devices as image size and throughput requirements have grown. First generation scanners, FIG. 1a, utilize a source 10, which may have a collimator to shape the beam, and a single detector element 11 to acquire data for a CT image. The part 12 is translated laterally past the source and detector at a first view angle, rotated and scanned laterally at the second view angle, and so on until many view angles over 180 degrees have been covered and a parallel beam data set has been acquired point by point in series. Second generation scanners, FIG. 1b, use a number of discrete detectors aimed at the source at different angles over a given range, $\theta_R$, to allow acquisition of data a number of view angles simultaneously. Multiple element detector 13 has wide element spacing and the four view angles cover $\theta_R$. Part 12 is translated and scanned past the source and detectors to collect all the data for the angles represented. It is then rotated by angle $\theta_R$, and scanned laterally again for the new range of view angles. The process is repeated N times until $N\theta_R$ is greater than or equal to 180 degrees.

Third generation CT scanners, FIG. 1c, speed up the process significantly by using a linear array of detectors to acquire all the data at a fixed view angle simultaneously. Multiple element detector 14 has narrow element spacing and the size of part 12 is smaller than the field of view of the detector. Only rotational scanning of the part 12 through 360 degrees is required to acquire the data for the various view angles. However, the data is acquired in fan beam configuration, and the detector array must be wide enough to span the part.

SUMMARY OF THE INVENTION

An object of the invention is to maintain the speed advantages of a third generation imaging system even when the detector is not wide enough to span the part. Another object is to provide an improved x-ray detector and scanning configuration which provides rapid data acquisition capability for large industrial parts, in both computed tomography and digital radiography imaging.

Yet another object is to provide a technique of synthesizing a larger detector array whereby a smaller detector array may be utilized in the scanning of parts of many sizes.

Still another object is the provision of a translate rotation scanning motion of an object relative to an x-ray source and detector, and image reconstruction procedures using such data sets.

One aspect of the invention is an improved scanning and data acquisition method for CT and DR imaging, using a fan beam x-ray source and a detector array which has a width insufficient to span an object. The method comprises successively scanning the object and acquiring partial x-ray data sets at a plurality of relative positions of the object and the x-ray source and detector array, the object being translated and rotated relative to the source and detector at every position with respect to a preceding position. The total number of positions depends on the width of the detector array and the object field of view. The method further comprises combining the partial data sets, which cover the entire field of view, to yield a complete x-ray data set to reconstruct an image of the object.

To acquire x-ray data for CT imaging, scanning is accomplished by rotating through 360 degrees at all of the positions. A feature of this method is that the combining of the partial data sets may begin and image reconstruction started after all the data for a first view angle has been received; it is not necessary to wait until the end. Another feature is that the combining of data may include selecting x-ray data for only those ray paths that pass through the object field of view and a given portion of the field of view. Ray paths outside the field of view, for instance, are not used.

Another aspect is an improved translate and scanning method for use with an x-ray imaging system including a x-ray source which generates a fan beam having a fan angle, and a linear detector array which has a width less than that of an object to be imaged. The method as applied to a dual scan system comprises placing the object at a first position relative to the source and detector array, scanning and acquiring a partial x-ray data set, moving the object to a second position and rotating and translating the object relative to the source and detector, and scanning and acquiring another partial x-ray data set. These partial data sets covering the object field of view are combined to yield a full data set to reconstruct a complete image of the object.

An illustrative embodiment synthesizes a much larger detector array that is symmetrical with the object. In the first relative position, using the smaller detector, the object is translated to the right of the fan beam center line and rotated through a predetermined angle, and in the second relative position the object is translated to the left of the fan beam center line and rotated a like amount in the opposite direction. In both positions data for CT imaging is acquired by then rotating the object through 360 degrees. DR imaging data is acquired by making vertical scans at each of the two positions.

BRIEF DESCRIPTION OF THE DRAWINGS

FIG. 2 is a diagram used to explain a first embodiment of the third generation translate/rotate inspection system.

FIG. 3 illustrates the translate/rotate x-ray scanner and determination of the rotation angle $\phi_0$.

FIG. 4 illustrates the foregoing system and translating and rotating the object relative to the stationary source and detector.

FIG. 5 is a diagram of the preferred embodiment of the translate/rotate CT and DR scanner.

FIG. 5 is a diagram of the preferred embodiment of the translate/rotate CT and DR scanner.

FIG. 6 shows the preferred system and translating and rotating the object relative to the stationary source and detector.

DETAILED DESCRIPTION OF THE INVENTION

Figure 1C:
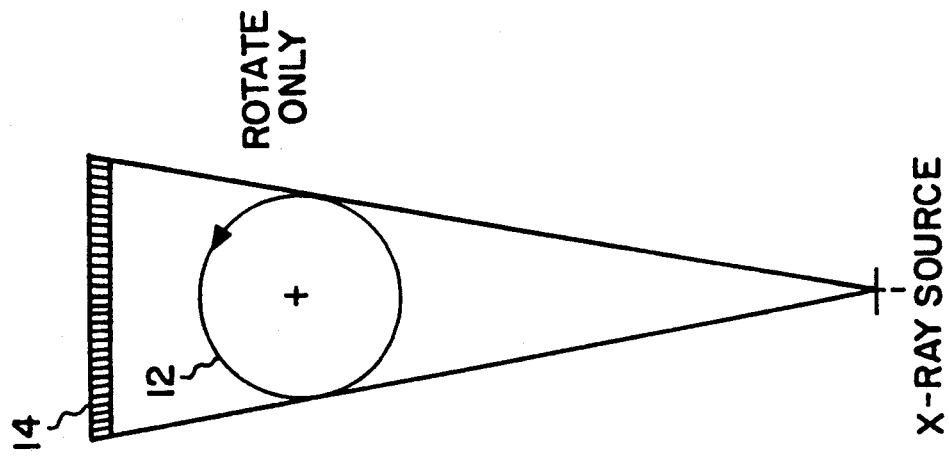
FIG. 1c shows a prior art third generation CT scanner utilizing a detector array with narrow element spacing.

The x-ray imaging system in FIG. 2 has a flat detector array 15 that is not wide enough to span an object 16. Suppose, for example, that a 20 inch diameter part must be scanned with a 12 inch detector. This requirement may arise in various ways; only a 12 inch detector may be available, it may be difficult or impossible to manufacture a larger detector, or data acquisition electronics may be unavaiable for more than the number of elements in a 12 inch detector. The CT scan is accomplished by rotating the object 16 through a full 360 degree rotation at positions 1 and 2 relative to the fan beam x-ray source 17 and detector 15. In position 1 the source is at point B and the detector extends from points D to E. The source is at point C in position 2 and the detector is moved and extends from points D' to E'. This assumes that the object 16 is stationary and the x-ray source and detector array are moved relative to it, but the object may be moved relative to the source and detector. This dual scan provides a full x-ray data set for CT imaging of the full 20 inch diameter object. However, combining the two data sets to achieve a suitable CT image of the object is not simple. As can be seen from FIG. 2, a straightforward combination which matches the data at the front of the object 16, at point G, results in misalignment at the detector of density contributions of various points within the sector defined between point G and points A1 and A2 at the rear of the object. This invention, therefore, also provides a method for combining the data sets from the two data acquisition positions so that misalignment is avoided and standard CT data is available. Standard DR x-ray data is produced when the object is scanned vertically through the fan beam at one view angle in both positions.

Consider the data which is acquired at position 1 of the source and detector. The object field of view in this discussion is a circle completely enclosing the object and is the same as the periphery of object 16 in this figure. The object or part may have many shapes, but always fits inside the circle defining the field of view. The minimum detector width which can be used for a two position data acquistion scan is determined by the requirement that the extreme rays detected by detector 15 pass through the outside limit of the 20 inch field of view at one side and through the lower center (x=0, y=−10) of the field of view at the other side. This criterion also determines the offset in the x direction of the source and detector for position 1. Position 2 is symmetric on the other side of x=0; the extreme detected rays pass through the outside limit of the 20 inch field of view at the other side, and through the lower center of the field of view at point G.

The data required to complete the scan with the source 17 and detector 15 at position 1 is that which would be acquired if the detector array were wide enough to span the entire object, i.e., if the detector array stretched from points D to F instead of from D to E. Point F is determined by drawing the dashed line from source position 1 tangent to the object field of view 16. The missing data is that which would be acquired on a series of lines through the object field of view 16 with slopes defined by the lines through the source and the various missing detector elements. However, data over lines with these slopes is acquired in position 2 of the source and detector array, providing the object is first rotated through a small angle $\phi_0$ before scanning begins. This is illustrated in FIG. 3 which shows the same two position x-ray imaging system except that the linear detector array 19, having the same length as from D to E in FIG. 2, is illustrated in both position 1 and 2. The array 19 in position 2 is the same distance from the source as in position 1 but is shown at a slightly larger distance for clarity. In particular, this x-ray data not acquired in position 1 is acquired in position 2 at rotation angle $\phi_0$ which puts the line from G to A1 along a ray from source position C to a detector element of detector array 19 in position 2, line G' to A1'. Angle $\phi_0$ is slightly less than the full fan angle $2\gamma$ of fan beam 18, and its value depends in detail on the geometry of the inspection. It is determined iteratively by rotating the field of view circle through various angles and determining the best alignment of the line between the rotated line G-A1 with the lines between source position C and the relevant detector elements of detector array 19 in position 2.

The partial x-ray data set which is acquired in this fashion at position 2 corresponds to exactly the correct range of slopes of lines from source to detector required to acquire the data missing from position 1 without misalignment.

Consider a specific example in which inspection of a 20 inch diameter field of view is to be carried out with a 12 inch or smaller detector array. For this case, the minimum detector size which can be used is a 1070 element detector array roughly corresponding to a 10.7 inch detector array. The Y direction distance from x-ray source 17 to the center of object field of view 16 is 81.25 inches and to detector array 19 is 95 inches. The offset $\Delta x$ from source 17 to the center for position 1 is −4.682 inches, and the offset $\Delta x$ for position 2 is 4.682 inches. The maximum fan angle is $2\gamma = 7.54°$, and the rotation angle $\phi_0 = 6.61°$. The 1970 individual detector elements are of equal size and spacing when considered as a linear array. However, from the geometry, it will be appreciated that, when considered in terms of angular distance, detector element size and spacing are nonuniform. Appropriate interpolation is required to complete the data set in position 2 at the spacing required in position 1. Thus, a total of 950 additional detector elements would be required to complete the scan in position 1. In position 2, 938 data points are acquired to complete the scan.

The procedure just described for using x-ray data acquired at position 2 to complete the partial data set at position 1 can be used for both DR and CT imaging. In DR imaging, the object 16 is scanned vertically through the x-ray fan beam 18 at one view angle in position 1 of the x-ray source 17 and detector array 19. Then, source and detector array are moved to position 2, the object 16 is rotated through angle $\phi_0$ and the object is scanned vertically at the one view angle at position 2. Refer to U.S. Pat. No. 4,803,639, the disclosure of which is incorporated herein by reference. The partial x-ray data sets required at positions 1 and 2 are combined in the manner described, yielding a complete data set that covers the entire field of view, and the complete DR image of the object is displayed. For CT imaging, the object 16 is rotated through a full 360 degree rotation at position 1, the source 17 and detector array 19 are moved to position 2, and the object 16 is again rotated through a full 360 degree rotation. The two data sets cover the entire field of view of object 16 and are combined as just described, and the complete CT image is displayed. The rotation of the object 16 through a full 360° at both position 1 and position 2 provides a full data set for CT reconstruction using standard algorithms such as filtered backprojection. In FIG. 3 the translate rotate scanning motion of the object 16 relative to the x-ray source 17 and detector 19 is obtained by rotating the object and translating the source and detector array. It is often more convenient, as illustrated in FIG. 4, to keep the source 17 and detector array 19 stationary and translate and rotate the object 16. The object is scanned in the first position and x-ray data covering at least half the object field of view 16 is acquired, then the object 16 is moved to the second position and rotated through angle $\phi_0$. The object is scanned and x-ray data covering at least the other half of the field of view is acquired. These two data sets are combined in the same way to yield a full data set for image reconstruction.

The translate rotate x-ray system configuration in FIG. 2 synthesizes x-ray data from a detector 15 which extends from D to F with the x-ray source 17 at point B. This configuration is suitable for DR imaging but is less desirable for CT imaging because data is synthesized from a detector which is asymmetric as to the object 16. This makes for a complex rebinning of x-ray data for the CT reconstruction algorithms. The preferred embodiments of the translate rotate x-ray system and method of scanning and imaging are shown in FIGS. 5 and 6, and are desirable for both CT and DR imaging. This approach synthesizes data from a detector that is symmetric with respect to the object being imaged. X-ray fan beam source 20 is at x=0 and the synthesized detector 21 completely spans an object 22. The detector 21 is wide enough that extreme rays tangent to the object 22 and its field of view (the same) at either side are detected by the endmost elements.

A minimum detector width of a smaller linear detector array 23 which can be used for a two position data acquisition scan is, as before, determined by the requirement that the extreme rays of the fan beam 24 that are detected are tangent to the object field of view 22 at the one side, and pass through the lower center 25 of the field of view at the other side. This criterion determines the offset $\Delta x$ of the source 20 and detector array 23 for position 1. Position 2 is symmetric on the other side of x=0. At position 1 of the source 20 and detector array 23, object 22 is rotated slightly counterclockwise through an angle $\gamma_r$, to make the ray paths from position 1 of the source 20 match the ray paths of the larger detector 21 to be synthesized. The rotational angle $\gamma_r = \gamma - \gamma_2$, where $\gamma$ is half the fan angle for the large synthetic detector 21 and $\gamma_2$ is half the fan angle for the physical detector 23. At position 2 the object is rotated by a like amount in the opposite, clockwise direction. The scanning and data acquisition procedures are the same and reviewed later. The first scan is done with the source 20 and detector array 23 at position 1 and object 22 rotated counterclockwise through the angle $\gamma_r$. The second scan is begun with the source and detector array at position 2 and the object rotated clockwise through angle $\gamma_r$.

FIG. 6 shows the same x-ray system and translating and rotating the object 22 relative to the stationary source 20 and detector array 23. Object 22 is translated right and left of the x-ray fan beam center line 25' and rotated. Translation of the object on the arc of a circle or other path may also be appropriate under certain circumstances. A more detailed description of the scanning and data acquisition for CT imaging is given in the flowchart of FIG. 7, which shows operating steps 26–30. Combining the x-ray data from both scans may begin before all the data is acquired, and image reconstruction started. Steps 26 and 27 are to translate object 22 to the right of center line 25' by $\Delta x$ and rotate counterclockwise to angle $-\gamma_r$. The object is rotated through full 360 degree rotation to acquire data at many view angles covering 360 degrees for CT imaging. Object 22 is moved to its second position relative to the source and detector. As seen in steps 28 and 29, the object is translated to the left by $2\Delta x$ and rotated clockwise through angle $2\gamma_r$. Rotation over a full 360 degrees is started and after acquiring data for the first view angle, the data from the first and second scans is combined and image reconstruction is started. The procedure in step 30 is to acquire data for other view angles in sequence, combining the two data sets as data is received and processed, and continuing image reconstruction as soon as the combined data is available.

Figures 7, 8:
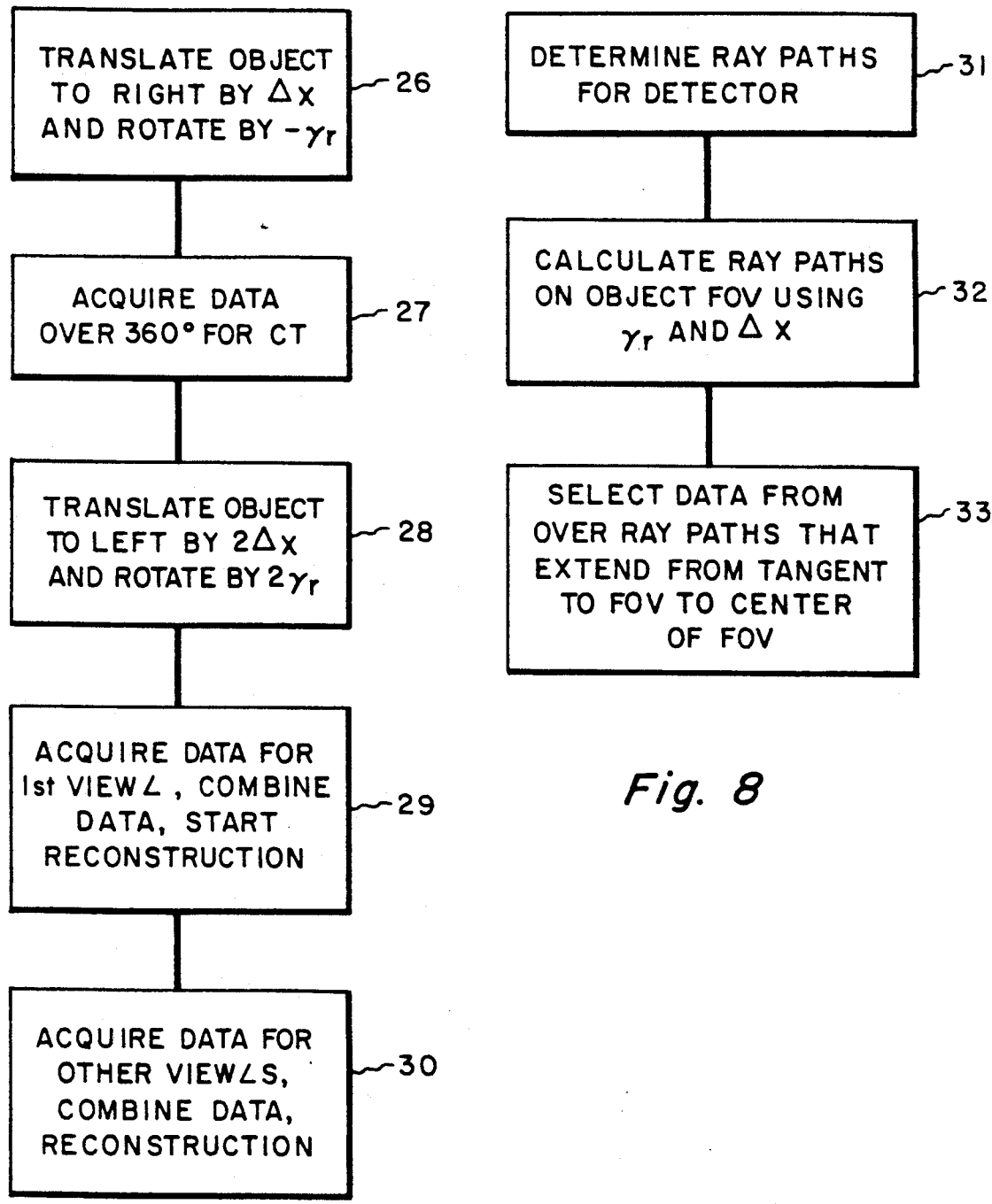
FIG. 7 is a flowchart of operating steps for the FIG. 6 system.
FIG. 8 is a flowchart detailing how the x-ray data from the position 1 and 2 scans is combined to obtain a full data set.

The method of combining the x-ray data received at one position of the object relative to the source and detector is given in the flowchart in FIG. 8. Steps 31–33 apply to combining data for the left hand side of the object, and the same three steps are followed to combine the right hand side data. Ray paths for the detector 23 are determined, that is, the ray paths from source 20 to every detector element in array 23 are calculated. Ray paths on the object field of view 22 using $\gamma_r$ and $\Delta x$ are then calculated. As before, the object 22 is represented by a circle and its field of view is the same circle. Sometimes the detector array that is used is wider than the minimum width that may be required and excess x-ray data is acquired. If this is the case, data is selected from over the ray paths that extend from the tangent to the field of view to the center of the field of view.

Figure 9:
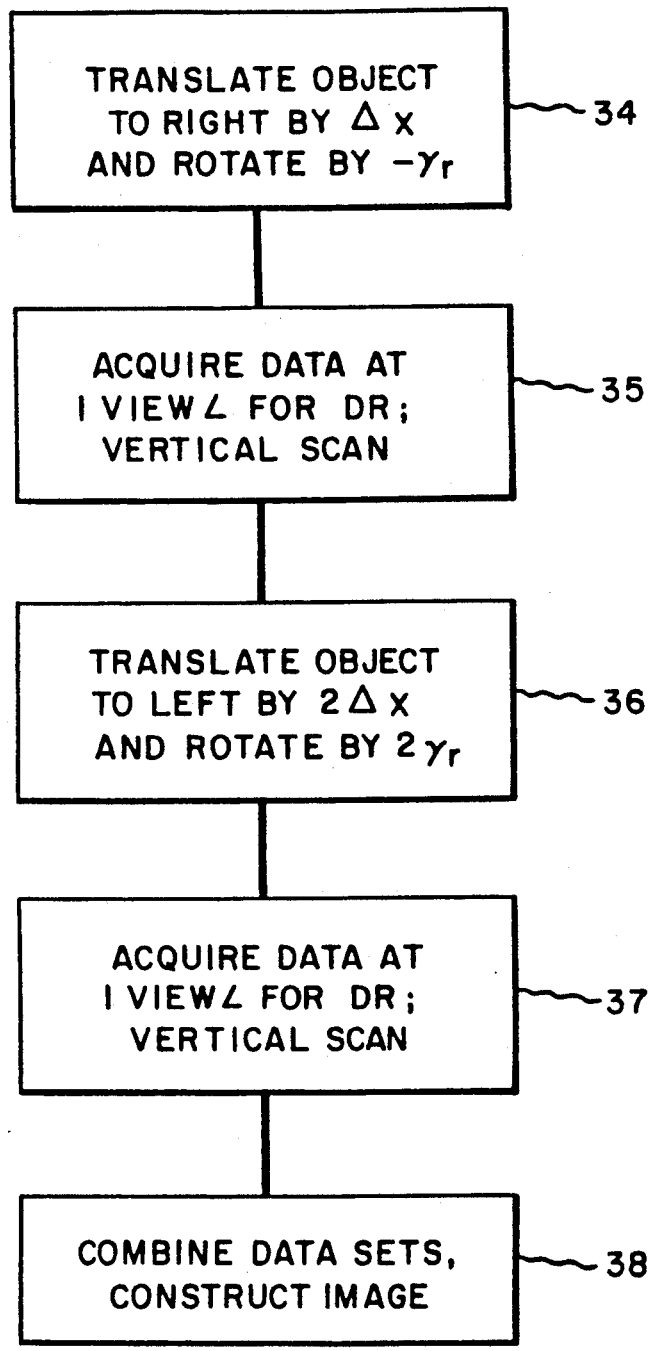
FIG. 9 is a flowchart showing operation of the FIG. 6 system as a DR scanner.

The translate rotate scanning and data acquisition method for DR imaging, using the x-ray system in FIG. 6, is described at steps 34–38 in the flowchart of FIG. 9. Object 22 is translated to the right by $\Delta x$ and rotated counterclockwise through angle $-\gamma_r$. X-ray data is acquired at one view angle as the object is scanned vertically through fan beam 24. Object 22 is translated to the left by $2\Delta x$ and rotated clockwise through angle $2\gamma_r$. Second position data is acquired at the one view angle by a second vertical scan through the fan beam. The first position and second position data sets are combined as was done for CT, and a complete DR image is reconstructed.

Scans of large parts using more than two detector positions allow even larger parts to be scanned. Position offsets, rotation angles, and the like are determined from similar considerations as in the two position scan. An alternate way of looking at the invention is that a wide variety of objects and parts, smaller and larger than the width of the detector array, can be scanned using the same detector array.

Figure 10:
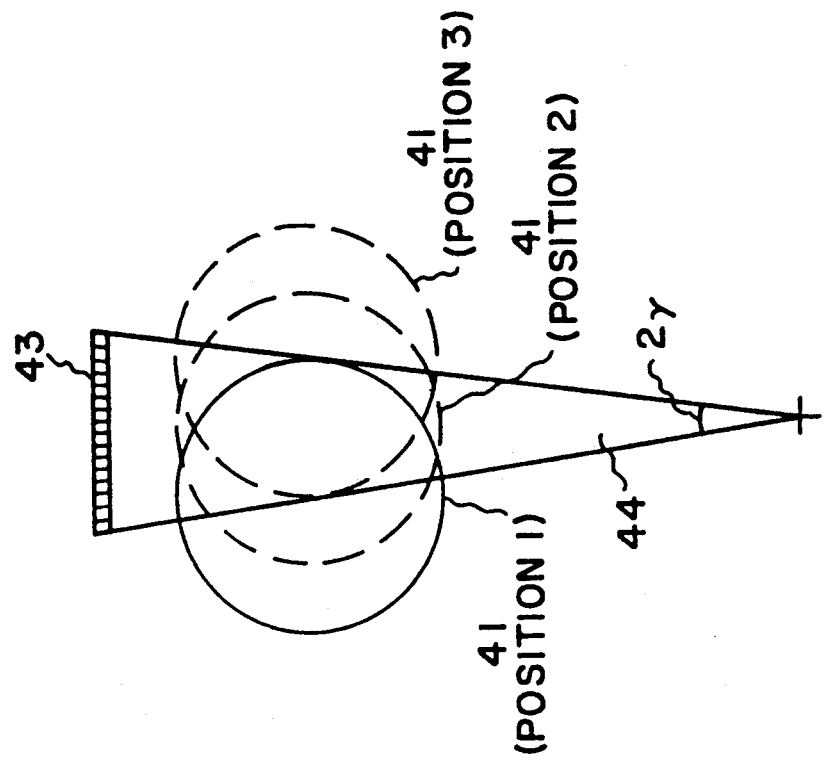
FIGS. 10 and 11 illustrate a multi-position translate/rotate CT scanner in which the source and detector are translated and the object rotated, and the object is both translated and rotated.
Figure 11:
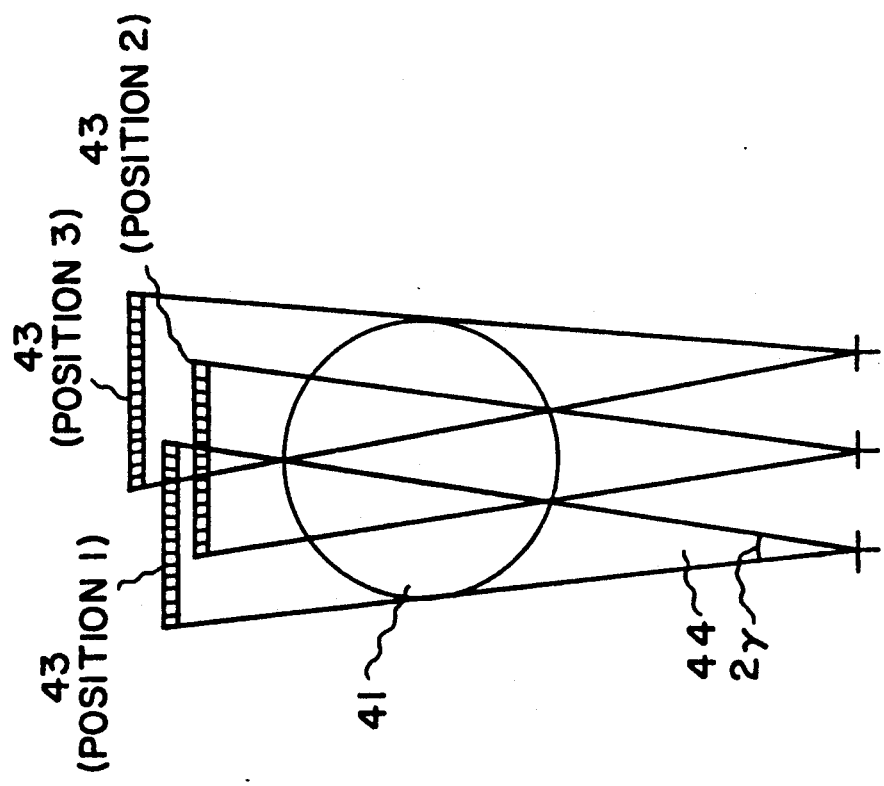

FIGS. 10 and 11 illustrate a three position translate rotate system for scanning a larger object 41 and field of view than in the previous figures. X-ray fan beam source 42 and detector array 43 may be the same as the source and detector in FIGS. 5 and 6. The first scan is done with the source 42 and detector 43 translated to the left and the object 41 rotated through angle $\gamma_r$, the second scan with the source and detector at the center and the object rotated back, and the third scan with the source and detector translated to the right and the object rotated clockwise through rotation angle $\gamma_r$. FIG. 11 shows the scanning configuration for a system in which the source 42 and detector array 43 are stationary and the object is moved from a first to a second and third position and rotated as just described. For CT imaging data is acquired over 360 degrees in all three positions. Data acquisition for DR imaging requires a vertical scan at one view angle at the three positions. The number of scanning positions, two or three or more, is determined by dividing the diameter of the object by the detector field of view diameter. For the example of a 20 inch diameter object and a 12 inch detector field of view, the quotient is 1.6, and 2 positions are required.

Conventional CT image reconstruction using filtered backprojection algorithms and a complete data set over a full 360 degrees has been described. Other reconstruction algorithms which require data over a 180 degree angular range or a 180 degree plus fan angle set may be used. In the former the data is sorted into a parallel beam data set and reconstructed with a parallel beam reconstruction algorithm. The latter uses iterative filtered backprojection to reconstruct the 180 degree$+2\gamma$ data set. Refer to the technical paper by K. C. Tam, "Reducing the Fan-Beam Scanning Angular Range", Phys. Med. Biol., 1988, Vol. 33, No. 8, pp. 955–967. These techniques may allow a speed-up of an additional factor of two in the data acquisition time.

Figure 1B:
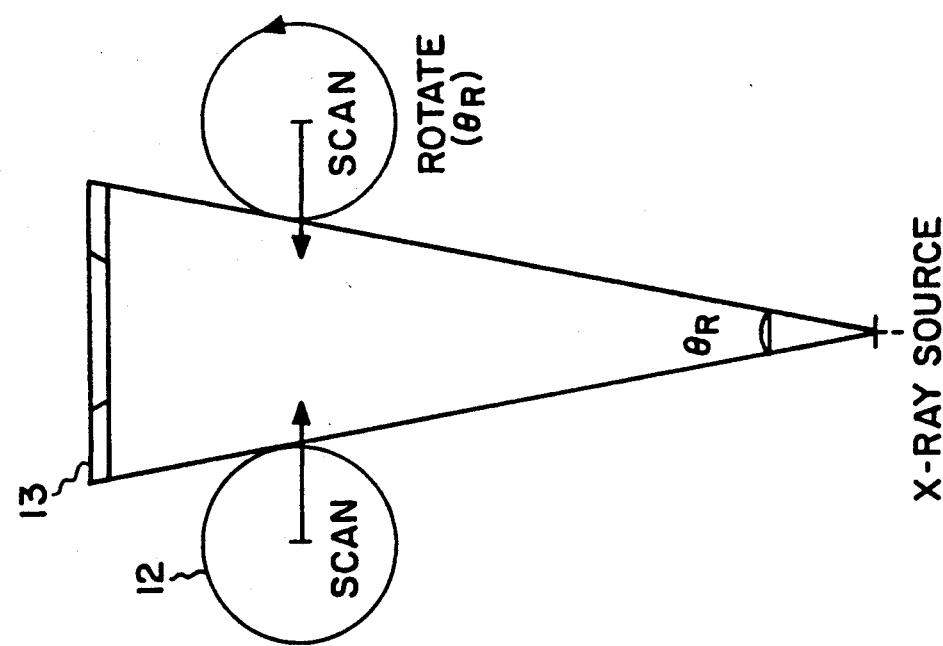
FIG. 1b shows a prior art second generation CT scanner having a detector array with wide element spacing.
Figure 1A:
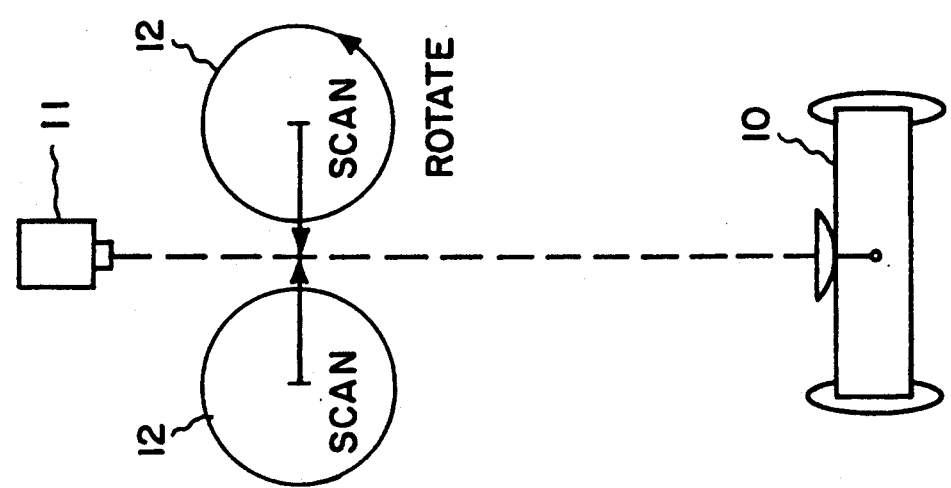
FIG. 1a shows a prior art first generation CT scanner having a single detector element.

A comparison of scan speeds between the improved third generation translate/rotate configuration of this invention with the conventional second generation configuration in FIG. 1b shows that the scan time is considerably less. A specific example having a two position scan was three times faster than the prior art method.

While the invention has been particularly shown and described with reference to preferred embodiments thereof, it will be understood by those skilled in the art that various changes in form and details may be made without departing from the spirit and scope of the invention as defined in the appended claims.

What is claimed is:

1. An improved scanning and data acquisition method for digital radiography (DR) and computerized tomography (CT) imaging of an object within a field of view, said method comprising:
   providing a fan beam x-ray source and a detector array having a width insufficient to span the field of view,
   successively scanning said object and acquiring partial x-ray data sets at a plurality of relative positions of said object and said x-ray source and detector array, said object being translated and rotated through a rotation angle relative to said x-ray source and detector array at every position with respect to a preceding position, the rotation angle selected to achieve alignment of the partial x-ray data sets; and
   combining said partial data sets to yield a full data set covering the entire field of view from which to reconstruct an image of said object.

2. The method of claim 1 wherein said scanning comprises rotating said object through 360 degrees at all of said positions, at multiple view angles in sequence, to acquire the partial data sets for CT imaging.

3. The method of claim 2 wherein the combining of the partial data sets begins and image reconstruction is started when all of the x-ray data for a first view angle is acquired.

4. The method of claim 1 wherein said scanning comprises scanning said object vertically through the x-ray fan beam at all of said positions to acquire the partial data sets for DR imaging.

5. The method of claim 1 wherein said combining comprises selecting x-ray data for only those ray paths that pass through the object field of view.

6. An improved translate and rotate scanning method for x-ray imaging of an object within a field of view, said method comprising:
   providing a x-ray source which generates a fan beam having a fan angle, and a linear x-ray detector array whose width is insufficient to span the field of view;
   placing the object at a first position relative to said source and detector array, scanning and acquiring a partial x-ray data set;
   moving said object to a second position with said object rotated and translated relative to said source and detector array, scanning and acquiring another partial x-ray data set;
   moving said object to at least one other position and rotating and translating said object relative to said source and detector array, scanning and acquiring at least one other partial x-ray data set; and
   combining said partial data sets, which cover the entire field of view, to yield a full data set to reconstruct a complete image of said object.

7. The method of claim 6 wherein said scanning in every position comprises rotating said object through 360 degrees to acquire computerized tomography (CT) data.

8. The method of claim 6 wherein said scanning in every position comprises scanning said object vertically through the x-ray fan beam at one view angle to acquire digital radiography (DR) data.

9. An improved translate and rotate scanning method for x-ray imaging comprising:
   providing a x-ray source which generates a fan beam having a fan angle, and a linear x-ray detector array which has a width less than that of an object to be imaged;

placing said object at a first position relative to said source and detector array, scanning and acquiring an x-ray data set;

moving said object to a second position with said object rotated and translated relative to said source and detector array, scanning and acquiring another x-ray data set; and combining said data sets to yield a full data set to reconstruct a complete image of said object.

10. The method of claim 9 wherein said scanning comprises rotating said object through 360 degrees at said first and second positions to acquire the data sets for computerized tomography (CT) imaging.

11. The method of claim 9 wherein said scanning comprises scanning said object vertically through the x-ray fan beam at said first and second positions to acquire the data sets for digital radiography (DR) imaging.

12. The method of claim 9 wherein, at said first position, said object is translated to the right of a fan beam center line and rotated counterclockwise through a predetermined angle, and at said second position is translated to the left of the fan beam center line and rotated clockwise through the same predetermined angle.

13. The method of claim 12 wherein said scanning at said first and second positions comprises rotating said object through 360 degrees and multiple view angles to acquire the partial data sets for computerized tomography (CT) imaging.

14. The method of claim 13 wherein said combining of the partial data sets begins and image reconstruction is started after acquiring x-ray data at a first view angle with said object in said second position.

15. The method of claim 14 wherein said combining comprises selecting x-ray data for only those x-ray paths that pass through the object field of view.

16. The method of claim 9 wherein said scanning comprises scanning said object vertically through the x-ray fan beam at one view angle in said first and second positions.

* * * * *

UNITED STATES PATENT AND TRADEMARK OFFICE
CERTIFICATE OF CORRECTION

PATENT NO. : 5,032,990

DATED : July 16, 1991

INVENTOR(S) : Jeffrey W. Eberhard and Kwok C. Tam

It is certified that error appears in the above-identified patent and that said Letters Patent is hereby corrected as shown below:

On the title page,  RE:  ATTORNEY, AGENT, OR FIRM

Please change Marilyn Glaubensklee; James C. Davis, Jr.; Paul R. Webb, II to:

Paul R. Webb, II; James C. Davis, Jr.

Signed and Sealed this

Twenty-second Day of December, 1992

*Attest:*

DOUGLAS B. COMER

*Attesting Officer*   *Acting Commissioner of Patents and Trademarks*